United States Patent
Pirie-Shepherd et al.

(10) Patent No.: US 10,254,286 B2
(45) Date of Patent: Apr. 9, 2019

(54) METHODS FOR DETECTING 5T4-POSITIVE CIRCULATING TUMOR CELLS AND METHODS OF DIAGNOSIS OF 5T4-POSITIVE CANCER IN A MAMMALIAN SUBJECT

(71) Applicants: Pfizer Inc., New York, NY (US); Epic Sciences, Inc., San Diego, CA (US)

(72) Inventors: Steven Pirie-Shepherd, Cardiff, CA (US); Hans-Peter Gerber, Montclair, NJ (US); Dena Marrinucci, San Diego, CA (US); Eric Tucker, San Diego, CA (US)

(73) Assignees: Pfizer Inc., New York, NY (US); Epic Sciences, Inc., La Jolla, CA (US)

( * ) Notice: Subject to any disclaimer, the term of this patent is extended or adjusted under 35 U.S.C. 154(b) by 0 days.

(21) Appl. No.: 14/374,083

(22) PCT Filed: Jan. 22, 2013

(86) PCT No.: PCT/IB2013/050547
§ 371 (c)(1),
(2) Date: Jul. 23, 2014

(87) PCT Pub. No.: WO2013/111054
PCT Pub. Date: Aug. 1, 2013

(65) Prior Publication Data
US 2015/0017661 A1    Jan. 15, 2015

Related U.S. Application Data

(60) Provisional application No. 61/753,665, filed on Jan. 17, 2013, provisional application No. 61/590,066, filed on Jan. 24, 2012.

(51) Int. Cl.
*G01N 33/574* (2006.01)
*G01N 33/50* (2006.01)

(52) U.S. Cl.
CPC ... *G01N 33/57492* (2013.01); *G01N 33/5008* (2013.01); *G01N 33/5011* (2013.01); *G01N 33/57484* (2013.01); *G01N 2333/70589* (2013.01)

(58) Field of Classification Search
CPC .................................................. G01N 33/574

USPC ........................................................ 435/7.23
See application file for complete search history.

(56) References Cited

U.S. PATENT DOCUMENTS

| | | | |
|---|---|---|---|
| 4,391,904 A | 7/1983 | Litman et al. | |
| 5,869,053 A | 2/1999 | Stern et al. | |
| 8,044,178 B2 | 10/2011 | Boghaert et al. | |
| 8,309,094 B2 | 11/2012 | Gerber et al. | |
| 2004/0131241 A1 | 7/2004 | Curry et al. | |
| 2006/0088522 A1* | 4/2006 | Boghaert ............... | C07K 16/30 424/133.1 |
| 2009/0317836 A1 | 12/2009 | Kuhn et al. | |
| 2010/0233693 A1 | 9/2010 | Kopf-Sill et al. | |
| 2010/0255479 A1 | 10/2010 | Mikolajczyk et al. | |

FOREIGN PATENT DOCUMENTS

| | | | | |
|---|---|---|---|---|
| WO | 89/07947 A1 | 9/1989 | | |
| WO | 98/55607 A2 | 12/1998 | | |
| WO | 01/36486 A2 | 5/2001 | | |
| WO | 03/038098 A2 | 5/2003 | | |
| WO | 2007/089911 A2 | 8/2007 | | |
| WO | 2010/070276 A1 | 6/2010 | | |
| WO | 2010/111659 A1 | 9/2010 | | |
| WO | 2011/028905 A1 | 3/2011 | | |
| WO | 2011/050103 A1 | 4/2011 | | |
| WO | WO 2011/127219 | * | 10/2011 | ............... C12Q 1/68 |
| WO | 2012/006421 A2 | 1/2012 | | |

OTHER PUBLICATIONS

Cristofanilli et al, "Circulating Tumor Cells, Disease Progression, and Survival in Metastatic Breast Cancer", The New England Journal of Medicine 351:781-791 (2004).
Kraeft et al, "Reliable and Sensitive Identification of Occult Tumor Cells Using the Improved Rare Event Imaging System", Clinical Cancer Research 10:3020-3028 (2004).
Krivacic et al, "A rare-cell detector for cancer", Proceedings of the National Academy of Sciences USA 101 (29):10501-10504 (2004).
PCT International Search Report and Written Opinion for PCT/IB2013/050547 dated May 8, 2013.

* cited by examiner

*Primary Examiner* — Yan Xiao
(74) *Attorney, Agent, or Firm* — Carol A. McKeever (57) ABSTRACT

Methods are provided for detecting 5T4-positive circulating tumor cells in a mammalian subject. Methods of diagnosing 5T4-positive cancer in a mammalian subject are provided. The methods of detection or diagnosis indicate the presence of 5T4-positive metastatic cancer or early stage 5T4-positive cancer.

16 Claims, 3 Drawing Sheets

FIG. 1A

| 5T4 Expression | None | Low | Medium | High |
|---|---|---|---|---|
| H-Score Category | 0 | 1 | 2 | 3 |
| Epic 5T4 Expression Range | <3 | 3-8 | 8-20 | >20 |

FIG. 1B

| Cell Line | H-Score |
|---|---|
| MDA-MB-435 | 290 |
| NCI-H226 | 246 |
| NCI-H1975 | 197 |
| MDA-MB-361 | 137 |
| NCI-H522 | 103 |
| NCI-H2122 | 83 |

FIG. 2B

| Patient # | H-Score |
|---|---|
| 9322 | 69 |
| 1077 | 67 |
| 8225 | 68 |
| 8126 | 35 |
| 9394 | 97 |
| 9511 | 74 |
| 8424 | 47 |
| 1095 | 47 |
| 2079 | 74 |
| 8776 | n/a |
| 9497 | 15 |
| 1092 | 27 |
| 9390 | 19 |
| 9689 | n/a |
| 8667 | 47 |
| 8661 | n/a |
| 8425 | 61 |

METHODS FOR DETECTING 5T4-POSITIVE CIRCULATING TUMOR CELLS AND METHODS OF DIAGNOSIS OF 5T4-POSITIVE CANCER IN A MAMMALIAN SUBJECT

FIELD OF THE INVENTION

The present invention generally relates to a method for detecting 5T4-positive circulating tumor cells in a mammalian subject and to methods of diagnosing 5T4-positive cancer in a mammalian subject.

BACKGROUND OF THE INVENTION

The human 5T4 antigen is expressed in numerous cancer types and is substantially absent from normal tissues. Recently, high affinity monoclonal antibodies have been developed that specifically bind to the 5T4 antigen and cytotoxic agents have been conjugated to the 5T4 antibodies to form antibody drug conjugates for use in the treatment of 5T4-positive cancer (U.S. Pat. Nos. 8,044,178 and 8,309,094). It follows then that assessment of 5T4 expression could be a useful approach for identifying patients with 5T4-positive cancer. One approach would be the detection of the 5T4 antigen on circulating tumor cells (CTCs) in cancer patients.

Circulating tumor cells have been observed in the peripheral blood of patients with epithelial-derived cancers at ultra low concentrations (Kraeft et al., Clin Cancer Res 10: 3020-3028, 2004). The number of these cells has been shown to correlate with outcome for cohorts of metastatic breast cancer patients with progressive disease at the time of sampling (Cristofanilli et al., N Engl J Med 351: 781-791, 2004). For this reason, their characterization is of considerable biomedical interest in order to understand how these cells can travel via the blood stream to anatomically distant sites and form metastatic disease. Consequently, identifying CTCs associated with 5T4-positive cancer could provide a valuable diagnostic tool for patient identification.

Currently, CTCs are detected and analyzed primarily through immunocytochemical markers such as EpCam and the use of nuclear staining with DAPI (4',6-diamidino-2-phenylindole), a fluorescent stain that binds strongly to A-T rich regions in DNA. Although these approaches have been successful in enumerating and distinguishing CTCs, they differ from standard cytopathologic approaches as they omit the correlation with standard morphologic staining upon which diagnostic pathology is dependent. This creates difficulty in comparing CTCs to tumor cells from other sites obtained by routine diagnostic procedures. Although the ability to detect CTCs has the potential to aide in diagnostic and individualized treatment of cancer and efficacy of treatment, the understanding of the biology of CTCs could be improved by including standard cytopathologic methods. A need exists in the art to utilize detailed high resolution imaging of CTCs with conventional diagnostic pathology staining methods and bright-field microscopy to confer the potential of making a standard cytopathologic diagnosis of circulating 5T4-positive carcinoma cells and advancing the adoption of diagnosis using 5T4-positive CTCs in the clinic.

SUMMARY OF THE INVENTION

In one embodiment, the present invention provides a method for detecting 5T4-positive circulating tumor cells in a mammalian subject suspected of having 5T4-positive cancer comprising: testing a sample of blood from the subject, wherein the sample of blood comprises a cell population; mounting the sample of blood on a substrate; detecting the presence or absence of a first marker in the sample of blood that selectively binds to nucleated cells; detecting the presence or absence of a second marker in the sample of blood that binds to the circulating tumor cells; detecting the presence or absence of a third marker in the sample of blood that binds to the cell population or a subset of the cell population that are not determined to be tumor cells; detecting the presence or absence of a fourth marker in the sample of blood that selectively binds to the circulating tumor cells wherein said fourth marker is human 5T4 antigen; and, analyzing the cell population detected by the first, second, third, and fourth markers to identify and characterize the circulating tumor cells.

In another embodiment, the method for detecting the presence or absence of 5T4-positive circulating tumor cells in a mammalian subject suspected of having 5T4-positive cancer indicates the presence of early stage 5T4-positive cancer, a disease free state, or a non-measurable disease state in the mammalian subject.

In another embodiment, presence or absence of the circulating tumor cells in the blood sample indicates therapy management during 5T4-positive cancer therapy or cancer recovery.

In another embodiment, the cell population is a mixed cell population, the substrate is a planar substrate, a micro fluidic device, or a cartridge that holds an enriched population of cells.

In another embodiment, mounting the test sample on the substrate forms a biological monolayer.

In another embodiment, the cell population is analyzed by nuclear detail, nuclear contour, presence or absence of nucleoli, quality of cytoplasm, or quantity of cytoplasm, wherein said analyzing uses DAPI.

In another embodiment, the cell population is analyzed by measuring intact cells with a high nuclear to cytoplasmic ratio, intact cells with a low nuclear to cytoplasmic ratio, early apoptotic cells, or late apoptotic cells, and identifying the circulating tumor cells.

In another embodiment, the first marker, the second marker, the third marker, and the fourth marker is a fluorescent marker.

In another embodiment, the first marker is a cytologic stain to identify the circulating tumor cell by morphology, size, or nuclear to cytoplasmic ratio.

In another embodiment, the cytologic stain is DAPI.

In another embodiment, the cytologic stain is Wright-Giemsa stain.

In another embodiment, the second marker or the third marker is a cell-specific marker.

In another embodiment, the cell-specific marker is cytokeratin, CD45, M30, chemokine receptor, CXCR1, CXCR4, CD44, CD24, VEGFR-1, VEGFR-2, VEGFR-3, EGFR, or HuR.

In another embodiment, detecting the presence of the first marker, the presence of the second marker, the presence of the third marker, or the presence of the fourth marker, further comprises analyzing the cell population by cell attachment to the substrate, scanning the cell population on the substrate and imaging the cells by digital microscopy using relocation.

In another embodiment, the detection of 5T4-positive circulating tumor cells in the blood sample indicates presence of 5T4-positive cancer, wherein said cancer is selected from the group of consisting of carcinomas of the bladder, breast, cervix, colorectal, endometrium, kidney, liver, lung, esophagus, ovary, prostate, pancreas, skin, stomach, and testes. Preferably, said cancer is selected from the group consisting of colorectal, breast, pancreatic, and non-small cell lung carcinomas.

In another embodiment, the invention provides a method of diagnosing 5T4-positive cancer in a mammalian subject suspected of having 5T4-positive cancer comprising: testing a sample of blood from the subject, wherein the sample of blood comprises a cell population; mounting the sample of blood on a substrate; detecting the presence or absence of a first marker in the sample of blood that selectively binds to nucleated cells; detecting the presence or absence of a second marker in the sample of blood that binds to the circulating tumor cells; detecting the presence or absence of a third marker in the sample of blood that binds to the cell population or a subset of the cell population that are not determined to be tumor cells; detecting the presence or absence of a fourth marker in the sample of blood that selectively binds to the circulating tumor cells wherein said fourth marker is human 5T4 antigen; and, analyzing and quantifying the cell population detected by the first, second, third, and fourth markers to identify and characterize the circulating tumor cells.

In another embodiment, the invention provides a method wherein said quantification of the human 5T4 antigen on the circulating tumor cells is used to generate an H-score, wherein said H-score is used to select a 5T4-positive cancer patient population, and wherein said circulating tumor cells are characterized utilizing an optimized 5T4 4-color assay.

In another embodiment, the invention provides a method of screening an antibody-drug conjugate for treatment of 5T4-positive cancer in a mammalian subject suspected of having cancer comprising: administering a therapeutically effective amount of the antibody-drug conjugate to the subject suspected of having cancer; testing a sample of blood from the subject before and after treatment with the drug candidate, wherein the sample of blood comprises a cell population suspected of containing 5T4-positive circulating tumor cells; mounting the sample of blood on a substrate; detecting the presence or absence of a first marker in the sample of blood that selectively binds to nucleated cells; detecting the presence or absence of a second marker in the sample of blood that binds to the circulating tumor cells; detecting the presence or absence of a third marker in the sample of blood that binds to the cell population or a subset of the cell population that are not determined to be tumor cells; detecting the presence or absence of a fourth marker in the sample of blood that selectively binds to the circulating tumor cells wherein said fourth marker is human 5T4 antigen; and, analyzing the cell population detected by the first, second, third, and fourth markers to identify the circulating tumor cell in the sample of blood before treatment with the antibody-drug conjugate compared to after treatment with the antibody-drug conjugate, wherein a change in the ratio of the 5T4-positive circulating tumor cells to 5T4-negative circulating tumor cells in the sample of blood after treatment compared to the ratio of 5T4-positive to 5T4-negative circulating tumor cells in the sample of blood before treatment may indicate the efficacy of the antibody-drug conjugate in the reduction of 5T4-positive circulating tumor cells, wherein said antibody-drug conjugate compound is anti-5T4-A1-mcMMAF.

In another embodiment, the invention provides a method for detecting 5T4 positive circulating tumor cells in a mammalian subject suspected of having 5T4 positive cancer comprising: testing a sample of blood from the subject, wherein the sample of blood comprises a cell population; mounting the sample of blood on a substrate; detecting the presence or absence of a first marker in the sample of blood that selectively binds to nucleated cells wherein said first marker is DAPI; detecting the presence or absence of a second marker in the sample of blood that binds to the circulating tumor cells wherein said second marker is cytokeratin; detecting the presence or absence of a third marker in the sample of blood that binds to the cell population or a subset of the cell population that are not determined to be tumor cells said third marker is CD45; detecting the presence or absence of a fourth marker in the sample of blood that selectively binds to the circulating tumor cells wherein said fourth marker is human 5T4 antigen; and, analyzing the cell population detected by the first, second, third, and fourth markers to identify and characterize the circulating tumor cells.

DETAILED DESCRIPTION OF THE INVENTION

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

5T4 refers to the 5T4 oncofetal antigen, a 72 kDa highly glycosylated trans-membrane glycoprotein comprising a 42 kDa non-glycosylated core (see U.S. Pat. No. 5,869,053). Human 5T4 is expressed in numerous cancer types, including but not limited to carcinomas of the bladder, breast, cervix, colon, endometrium, kidney, lung, esophagus, ovary, prostate, pancreas, skin, stomach, and testes. Highly tumorigenic cells, also called cancer stem cells or tumor-initiating cells have been shown to have high levels of 5T4 expression (WO2010/111659). Anti-5T4 antibodies include antibodies that specifically bind the human 5T4 antigen (see U.S. Pat. No. 8,044,178).

"Biological monolayer" refers to a blood sample which may exist in various states of cell separation or purification. For example, the biological monolayer can be partially purified and contain mononuclear cells and other cells after lysis of red blood cell has occurred.

"Sorting the cell population prior to mounting the sample on a substrate" refers to removing a subset of the cell population from the sample, e.g., the blood sample. Sorting can occur by selective cell lysis and centrifugation of a subfraction of cells. Sorting can also occur using a fluorescent cell marker and fluorescence activated cell sorting. Cell sorting for a cell marker can occur as a positive selection for circulating tumor cells or as a negative selection to remove non-tumor cells.

The "substrate" holds the test sample, e.g., a blood sample containing cells mounted for detection and analysis. In one aspect, the substrate can be planar. In a further aspect, the substrate can have some curvature.

"Subject", "mammalian subject" or "patient" refers to any mammalian patient or subject to which the methods of the invention can be applied. "Mammal" or "mammalian" refers to human patients and non-human primates, as well as experimental animals such as rabbits, rats, and mice, and other animals. In an exemplary embodiment, of the present invention, to identify subject patients for treatment according to the methods of the invention, accepted screening methods are employed to determine risk factors associated with a targeted or suspected disease or condition, e.g., 5T4-positive cancer, or to determine the status of an existing disease or condition in a subject. These screening methods include, for example, conventional work-ups to determine risk factors that can be associated with the targeted or suspected disease or condition. These and other routine methods allow the clinician to select patients in need of therapy using the methods and formulations of the invention.

"Blood sample", "blood specimen", "test sample", and "sample of blood" are used interchangeably and are defined as an amount of blood withdrawn or taken from a subject, generally by a venipucture or transcutaneous puncture of a vein by a sharp rigid stylet or cannula carrying a flexible plastic catheter or by a steel needle attached to a syringe or catheter, for use in medical tests including diagnostic assays.

"Cancer", "malignancy", "solid tumor" or "hyperproliferative disorder" are used as synonymous terms and refer to any of a number of diseases that are characterized by uncontrolled, abnormal proliferation of 5T4-positive cells, the ability of affected 5T4-positive cells to spread locally or through the bloodstream and lymphatic system to other parts of the body (i.e., metastasize) as well as any of a number of characteristic structural and/or molecular features.

A "first marker", a "second marker", a "third marker", and a "fourth marker" identify a circulating tumor cell by a cytological stain or by a cell specific marker. The first maker is a cytological stain including, but are not limited to DAPI, Wright-Giemsa stain, or other cytological stains known in the art. See for example, B. F. Atkinson, Atlas of Diagnostic Cytopathology. $2^{nd}$ Edition, W.B. Saunders Company, Ed., 2003, incorporated herein by reference in its entirety. The second and third markers are cell specific markers including, but are not limited to, markers for cytokeratin, CD45, M30, chemokine receptor, CXCR1, CXCR4, CD44, CD24, vascular endothelial growth factor isoforms (VEGFR-1, VEGFR-2, VEGFR-3), epithelial growth factor receptor (EGFR), or mRNA stability factor HuR. The fourth marker refers to the 5T4 antigen.

These markers identify various cell types, including cells of hematopoietic origin, cytokeratins on epithelial cells, breast cancer cells, prostate cancer cells, CD44, cell surface receptor recognizing hyaluronic acid, chemokine receptors, such as CXCR1 or CXCR4.

"Sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

"Analyzing the cell population by nuclear detail, nuclear contour, presence or absence of nucleoli, quality of cytoplasm, or quantity of cytoplasm" and "analyzing the cell population by measuring intact cells with a high nuclear to cytoplasmic ratio, intact cells with a low nuclear to cytoplasmic ratio, early apoptotic cells, or late apoptotic cells, and identifying the circulating tumor cells" can occur utilizing techniques and analytical methods as described in B. F. Atkinson, id.

"Management of cancer therapy or cancer recovery" refers to in vivo or in vitro diagnostic tests to determine the stage of cancer progression or the effectiveness of a particular cancer therapy treatment.

"Circulating tumor cells (CTCs)" refer to intact tumor cells or clusters of tumor cells that are positive for pan cytokeratin and negative for CD45. CTCs also include cells that are positive for 5T4 and negative for CD45; cells that are both positive for pan cytokeratin and 5T4 and negative for CD45; and, cells that are morphologically consistent with malignant cells. Methods for categorizing and detecting CTCs have been reported previously (WO2011/028905, WO2011/050103, and US2009/0317836, herein incorporated by reference).

"H-Score" is a weighted score which sums the percentages of CTCs within each category (low, medium and high) multiplied by their respective category values, generating a score between 0 and 300.

There are several methods of detecting circulating tumor cells known in the art. The low level of concentration of malignant epithelial cells in blood samples, approximately one in $10^6$ to $10^7$ total nucleated cells makes them difficult to detect. Detection and enumeration of CTCs has been attempted with several methods including: PCR, flow cytometry, image-based immunologic approaches, immunomagnetic techniques, micro fluidic techniques, and microchip technology.

For example, the AdnaTest Breast Cancer® system utilizes reverse transcriptase-polymerase chain reaction (RT-PCR) to detect circulating tumor cells (AdnaGen AG, Langenhagen, Germany; OncoVista, Inc., San Antonio, Tex.). The test features a CTC-enrichment procedure that utilizes a proprietary mixture of immunomagnetic bead coated with one of three antibodies to epithelial surface antigens. The number of CTCs is then indirectly determined by a semi-quantitative RT-PCR method.

The CellSearch System™ (Veridex LLC, Warren, N.J.) was developed for the purpose of detecting CTCs in whole blood. The CellSearch system involves a technique of mixing a blood sample with iron particles coated with an antibody that attaches to epithelial cells. The epithelial cells are then distinguished from leukocytes by antibodies that have been tagged with a fluorescent dye so that the cancer cells can be easily distinguished and counted.

The OncoQuick™ (Greiner Bio-One-, Inc. Longwood, Fla.) is another testing system that has been developed to detect circulating tumor cells. This system is an enhanced density gradient system that combines density gradient centrifugation and the immune-based techniques.

A method of enumerating the number of CTCs in a sample from a patient comprising flowing said sample through a micro fluidic device that selectively enriches one or more circulating tumor cells is described in US Patent Application No. 2010/0233693, herein incorporated by reference. The micro fluidic device can enrich one or more CTCs based on size, affinity, deformability, or shape.

A method of isolating and analyzing CTCs utilizing a micro-channel device is described in US Patent Application No. 2010/0255479. This method provides for capturing biological targets from solution by pre-labeling or premixing a sample containing a CTC with a binding partner that specifically binds to the cells enhancing the capture of the CTC in a micro-channel device.

Each of the above mentioned methods of detecting circulating tumor cells requires a cell enrichment step. A distinguishing characteristic of the present invention is an enrichment-free assay that demonstrates the ability to identify significant numbers of CTCs in a majority of patients with 5T4-positive cancer.

An aspect of the present invention is generally related to a method for detecting 5T4-positive circulating tumor cells (CTCs) in a mammalian subject or a method of diagnosing an early stage 5T4-positive cancer in a mammalian subject. The present invention further relates to a method of screening a drug candidate compound in a mammalian subject for treatment of 5T4-positive cancer.

A method for detecting 5T4 positive CTCs in the mammalian subject is provided which comprises obtaining from the mammalian subject suspected of having cancer, a sample of blood comprising a mixed cell population suspected of containing CTCs, mounting the blood cells and CTCs on a substrate to form a biological monolayer, detecting in the biological monolayer a first marker that selectively binds to nucleated cells, detecting in the biological monolayer a second marker that binds to CTCs, detecting in the biological monolayer a third marker that binds to the mixed cell population or a subset of the mixed cell population, detecting in the biological monolayer a fourth marker that selectively binds to 5T4-positive cells, analyzing the cell population detected by the first, second, third, and fourth marker to identify CTCs; the presence of the CTCs in the sample of blood indicating the presence of 5T4-positive cancer or early stage 5T4-positive cancer in the mammalian subject. The presence or absence of the CTCs in the sample of blood can indicate the presence of a disease free state or a non-measurable disease state in the mammalian subject.

The method provides a cell attachment protocol to identify epithelial-derived cells within a blood sample, in conjunction with a method to detect 5T4-positive CTCs in blood of cancer patients. In this protocol, live white blood cells (WBCs) e.g., leukocytes, and other cells in the blood are isolated on a slide, for example, as a biological monolayer. Leukocytes include, but are not limited to: T-lymphocytes; monocytes, eosinophils, and neutrophils, involved in phagocytosis; and, basophils involved in inflammatory response.

The method further provides fluorescently labeling the attached WBCs and CTCs on specially coated adhesive slides. The cells are fluorescently labeled with a first marker that selectively binds to nucleated cells wherein said first marker is DAPI, a second marker that binds to the circulating tumor cells wherein said second marker is cytokeratin (CK) an essential component of CTCs, of a third marker that binds to the cell population or a subset of the cell population that are not determined to be tumor cells said third marker is CD45, and a fourth marker that selectively binds to the circulating tumor cells wherein said fourth marker is human 5T4 antigen. The slide is then scanned for sites of fluorescence and analyzed with high-performance computation that utilizes algorithms that weighs the cellular parameters detected by the first, second, third, and fourth markers to identify and characterize the circulating tumor cells.

The method further provides methods utilizing fluorescent microscopy and the cell attachment protocol to investigate the prevalence of CTCs in 5T4-positive cancer patients. An additional advantage of the method enables a pathologist to relocate and examine cells of interest for pathologic confirmation and characterization. In the present invention, the protocol further includes removing the coverslip and/or solubilizing the water-soluble mounting media on each fluorescently stained slide and re-staining the same cells using a second cell marker, e.g., a standard Wright-Giemsa staining, to provide additional insights into CTC morphology, size, and heterogeneity. Known $CK^+$ individual rare cells and rare cell clusters which were located by high performance computation and the cell attachment protocol can be evaluated morphologically. Although fluorescent images of CTCs have aided in their verified identification, the Wright-Giemsa stain has provided additional cytologic information about CTCs. In a further aspect of the invention, the method can be used to evaluate different cell markers that are specific for either a disease state, cell type, or cell state.

The ability to detect and characterize CTCs has the potential to aide in the diagnostic and individualized treatment of 5T4-positive cancer patients. Due to their rarity, special methods are required to investigate CTCs. The present invention provides a fluid phase biopsy approach that enables the use of standard cytopathologic methods for detailed morphologic characterization of CTCs in blood obtained from cancer patients and provides details of cytologic characteristics of a spectrum of CTCs without using surface protein-based enrichment. Nucleated cells recovered from whole blood are deposited onto adhesive slides, immunofluorescently labeled, and analyzed for 5T4-positive CTCs by digital microscopy. Coupling these techniques with routine staining methods enables identification and evaluation of CTCs using light microscopy. Using conventional pathologic methods to observe the cells, CTCs exhibit a high degree of inter- and intra-patient pleomorphism in whole blood preparations, and intact CTCs are identified with both high and low nuclear-to-cytoplasmic ratios along with CTCs exhibiting apoptotic hallmarks. Morphologic observations suggest that the full spectrum of cells present in primary and metastatic tumor sites may also be seen circulating in blood, and furthermore provide a possible framework of morphologic classification within which to investigate the properties of cell subsets involved in metastasis.

Automated Digital Microscopy. Coordinates of prospective cells are fed into the rare-event imaging system (REIS), a fully automated scanning digital microscopy system. The hardware components of the REIS and the proprietary scanning software have been described in detail elsewhere (Krivacic et al., Proc. Natl. Acad. Sci. USA 101: 10501-10504, 2004).

Measurements. Detected fluorescent objects are analyzed with software filter operations to differentiate rare cells from false positives. Because the cells are generally smaller than the laser-spot resolution (20 µm), the first filter passes all objects that are below a size threshold (20 µm). A second filter analyzes the ratio between the intensities of the fluorescence from different channels to eliminate homogeneous dye aggregates, a common artifact of immunofluorescence staining.

A sample can be prepared as a biological monolayer by drawing a sample of a biological fluid including, but not limited to, blood or parts of blood from a subject. In one aspect, the sample is a monolayer of cells. The fluid sample is treated with a fluorescent material, such as but not limited to a marker dye, that selectively bonds to different kinds of biological molecules, which may be on the surface or inside the cell, such as proteins, nucleic acids or other molecules. Suitable markers are known in the art for marking a number of different cell types of clinical interest, including selected cancer cell types, fetal cells, or other appropriate cells to be considered. Markers for numerous other cells such as brain cells, liver cells, as well as bacteria cells, among others can be developed. The material emits a characteristic output, such as fluorescence or phosphorescence, responsive to a selected excitation irradiation, such as irradiation by a selected wavelength or spectrum of light, x-ray irradiation, electron-becompleted this.am irradiation, or the like. The characteristic luminescence typically has a characteristic wavelength or spectral range of wavelengths. While dyes are the predominant tagging process, other techniques exist including the use of markers known as quantum dots and DNA nano-particle probes.

In another aspect of the invention, a method for obtaining a position of a rare cell, e.g., a 5T4-positive circulating tumor cell (CTC), within a biological monolayer is provided. See, for example, U.S. Application No. 2004/0131241, herein incorporated by reference. A slide which carries at least one rare cell and has reticle marks arranged at positions which form substantially a right angle, is positioned in a slide holder of a first imaging system. A first coordinate space of the imaging system is defined, and coordinates of the reticle marks in the first coordinate space are designated. A second coordinate space of a second imaging system is defined, and the coordinates of the reticle marks in the second coordinate space is designated. Using the designated coordinates of the reticle marks of the first coordinate space, the coordinate conversion parameters are computed. Thereafter, coordinates of at least one object in the first coordinate space are designated, and the first coordinate space coordinates of the object are converted into unique coordinates in a second coordinate space, using the coordinate conversion parameters.

Once the rare cell or CTC has been localized, the coverslip on the biological monolayer can be removed or the water-soluble mounting media can be solubilized on each fluorescently stained slide. The same cells can be re-stained using a second cell marker, e.g., standard Wright-Giemsa staining to provide insights into CTC morphology, size, and heterogeneity. Known cytokeratin positive (CK$^+$) individual rare cells and rare cell clusters can be located and evaluated morphologically. Although fluorescent images of CTCs have aided in their verified identification, the Wright-Giemsa stain has provided additional information about CTCs.

In a further aspect, this process can be used to evaluate different cell markers that are specific for either a disease, disease state, cell type, or cell state. Methods of the present invention will aid in characterization of CTCs. It enables high quality verification of CTCs from blood obtained from 5T4-positive cancer patients without enrichment, and provides insights into morphology and characteristics of CTCs.

The search for rare metastatic CTCs suggests that many CTCs are apoptotic and incapable of forming metastases and estimates that only 1 disseminated cancer cell in 10,000 can even establish a metastasis. Thus, detection, morphologic classification, and molecular characterization of these rare cells could target novel and directed therapies, demonstrating the clinical significance of CTCs.

Cancer Treatment

A method of cancer treatment is immunotherapy, wherein an antibody specific for the 5T4 antigen can be conjugated to a suitable drug, such as a cytotoxic or cytostatic agent, an immunosuppressive agent, a radioisotope, a toxin, or the like. The antibody drug conjugate (ADC) can be used to deliver a drug to a 5T4-positive tumor cell or cancer cell in a patient. ADCs for the treatment of 5T4-positives cancers have been disclosed in U.S. Pat. No. 8,309,094, herein incorporated by reference. Examples of ADCS are 5T4-A1-mcMMAF, 5T4-A1-vcMMAE, and 5T4-vc-MMAD, wherein 5T4-A1 is a humanized antibody that specifically binds the 5T4 antigen and MMAE, MMAE, and MMAD are auristatin derivatives. Auristatins have been shown to interfere with microtubule dynamics and nuclear and cellular division and have anticancer activity.

Diagnostic Assay

Figure 1A:
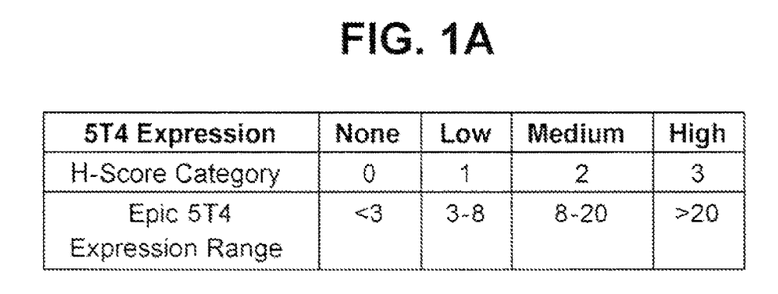
FIG. 1a compares the 5T4 expression range utilized in the calculation of an H-Score.
Figure 1B:
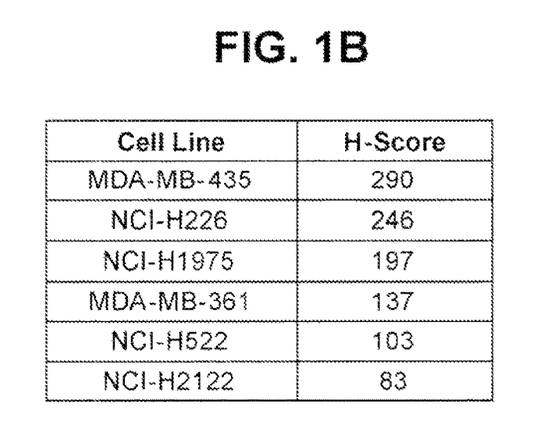
FIG. 1b provides calibrating cell lines depicting thresholds established for low, medium, and high expression of 5T4 in non-small cell lung cancer (NSCLC).

An embodiment of the present invention is illustrated in FIG. 1$a$ where the quantification of the 5T4 antigen on CTCs is used to generate an 'H-Score' by summing the percentages of CTCs within each category multiplied by their respective category values, generating a score between 0 and 300. As shown in FIG. 1$b$, the scoring system utilizes the 5T4 expression as determined by the optimized 5T4 4-color assay described in Example 1 using the panel of NSCLC cell lines selected based on 5T4 expression levels. These levels were confirmed by standard immunocytologic (ICC) staining experiments. These cell lines represent high (MDA-MB-435 and NCI-H226 cell lines), medium (NCI-H1975 and MDA-MB-361 cell lines) and low (NCI-H522 and NCI-H2122 cell lines) expression levels of 5T4. The mean expression level of 5T4 in each of these lines was used to establish thresholds for high, medium and low expression of 5T4 in this assay.

Figure 2A:
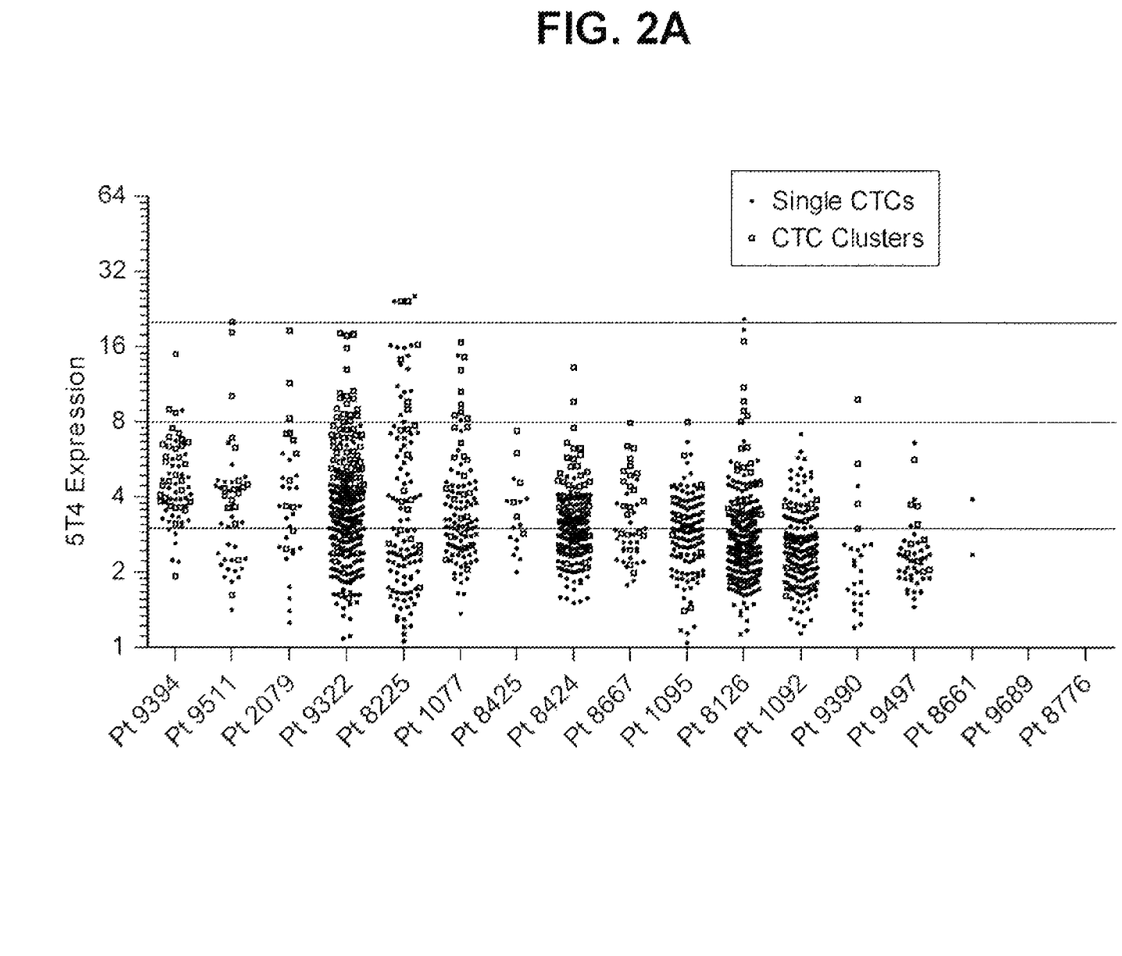
FIG. 2a shows the 5T4 expression scatter plot for both single CTCs and CTC clusters from NSCLC patient samples analyzed with the optimized 5T4 4-color diagnostic assay.
Figure 2B:
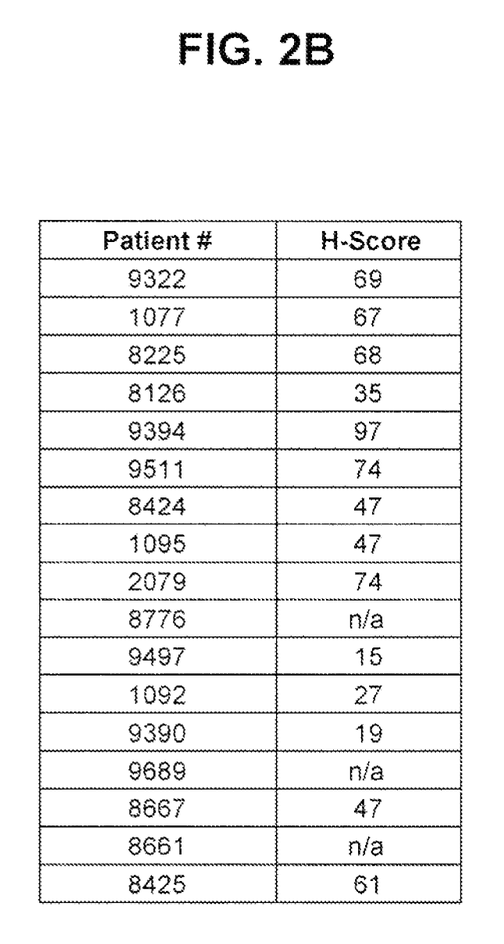
FIG. 2b shows data from 17 NSCLC patient samples analyzed with the optimized 5T4 4-color diagnostic assay and H-scores calculated using the calibrating cell lines.

In another embodiment of the present invention, cancer patients are screened for the presence of CTCs that express the 5T4 antigen utilizing the optimized 5T4 4-color diagnostic assay described in Example 1. This assay will help determine the level of 5T4 antigen expression on CTCs by enumerating and characterizing the CTCs, as well as, determining a correlation between CTC expression of the 5T4 target and 5T4 expression in the primary tumor. The 5T4 expression scatter plot shown in FIG. 2$a$ is for both single CTCs and CTC clusters as calibrated by the control cell lines. As shown in FIG. 2$b$, 17 non-small cell lung cancer (NSCLC) patient samples were processed with the optimized 5T4 4-color assay. Thus, the 5T4-4-color assay of the present invention is used to determine an H-score category that is then used in the H-score calculation. Ultimately, the diagnostic assay identifying 5T4 target expressing CTCs will be used to identify a treatable cancer patient population and as a means of monitoring the CTCs in the cancer patients during treatment with an ADC such as 5T4-A1-mcMMAF.

A further aspect of the present invention is to use the H-Score as a preliminary scoring system to characterize 5T4 on CTCs. As indicated above, the H-Score is a weighted score which sums the percentages of CTCs within each category multiplied by their respective category values, generating a score between 0 and 300. CTCs are divided into 4 categories (0-3) based on individual 5T4 expression as shown in FIG. 1$a$. A minimum of 10 CTCs must be present in order to calculate a reasonably useful H-Score.

For patients, H-Scores will be calculated in two ways: (1) Traditional H-Score (THS)—the average 5T4 intensity of every event (single CTC or CTC cluster) is counted as a single data point; (2) Cluster-Weighted H-Score (CWHS)—every CTC's average 5T4 intensity (single or within a cluster) is counted as a single data point.

An example of an H-Score calculation utilizing the values for the H-Score category and % CTCs per category is as follows: H-Score Category 0 (1.5% CTCs); H-Score Category 1 (15.0% CTCs); H-Score Category 2 (68% CTCs); H-Score Category 3 (15.5% CTCs). H Score=(1.5×0)+(15.0×2)+(68.0×2)+(15.5×3)=198

The H-score can then be utilized to select the patient population that would have the highest probability of success for treatment with an ADC such as 5T4-A1-mcMMAF or other 5T4 specific ADCs. FIG. 2b provides the H-Score calculation for 14 of 17 NSCLC patients utilizing the 5T4 4-color assay of the present invention.

In other embodiments, methods for treating cancer are provided, including identifying a patient that has 5T4 positive cancer by identifying 5T4 positive CTCs with the optimized 5T4 4-color assay, categorizing said patient by determining an H-score, and administering to a patient in need thereof an effective amount of an ADC that specifically binds a 5T4 positive cancer. Moreover the patient is monitored at intervals during the therapy for the presence of 5T4 positive CTCs utilizing the optimized 5T4 4-color assay. Detecting a decreased number of the 5T4-positive circulating tumor cells in the sample of blood after treatment with an ADC compared to the number of the 5T4-positive circulating tumor cells in a sample of blood before treatment with the ADC may indicate effectiveness of the antibody-drug conjugate compound in treating 5T4-positive cancer in the mammalian subject.

In another embodiment, analyzing the cell population utilizing the optimized 5T4 4-color assay to identify and characterize the circulating tumor cells in the test samples before treatment with the antibody-drug conjugate compared to after treatment with the antibody-drug conjugate, wherein a change in the ratio of the 5T4-positive to 5T4-negative circulating tumor cells in the sample of blood after treatment compared to the ratio of 5T4-positive to 5T4-negative circulating tumor cells in a sample of blood before treatment may indicate the efficacy of the antibody-drug conjugate in the reduction of 5T4-positive circulating tumor cells.

In some embodiments, the method of treating cancer includes identifying a patient that has 5T4-positive cancer by identifying 5T4-positive CTCs with the optimized 5T4 4-color assay and administering to said patient an effective amount of an ADC that specifically binds a 5T4 positive cancer in combination with a chemotherapeutic agent. The chemotherapeutic agent is that with which treatment of the cancer has not been found to be refractory. In some embodiments, the chemotherapeutic agent is that with which the treatment of cancer has been found to be refractory. The ADC can be administered to a patient that has also undergone a treatment, such as surgery for treatment for the cancer. In another embodiment, the additional method of treatment is radiation therapy. Moreover the patient is monitored at intervals during the therapy for the presence of 5T4 positive CTCs utilizing the optimized 5T4 4-color assay.

Detectable Label

The particular label or detectable group used in the assay can be detectable by spectroscopic, photochemical, biochemical, immunochemical, electrical, optical or chemical means. The particular type of label is not a critical aspect of the invention, so long as it does not significantly interfere with the specific binding of an antibody to the cellular marker on the cell or the circulating tumor cell used in the assay. The detectable group can be any material having a detectable physical or chemical property. Such detectable labels have been well-developed in the field of assays or immunoassays and, in general, most any label useful in such methods can be applied to the present invention. Thus, a label is any composition detectable by spectroscopic, photochemical, biochemical, immunochemical, electrical, optical or chemical means. Useful labels in the present invention include AlexaFlour® fluorescent dyes (Invitrogen), magnetic beads (e.g. Dynabeads™), fluorescent dyes (e.g., fluorescein isothiocyanate, Texas red, rhodamine, and the like), radiolabels, other imaging agents such as microbubbles (for ultrasound imaging), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads.

The label can be coupled directly or indirectly to the desired component of the assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include AlexaFlour® fluorescent dyes (Invitrogen), fluorescein and its derivatives, rhodamine and its derivatives, dansyl, umbelliferone, and the like. Chemiluminescent compounds include luciferin, and 2,3-dihydrophthalazinediones, e.g., luminol. For a review of various labeling or signal producing systems which can be used, see, U.S. Pat. No. 4,391,904 herein incorporated by reference.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple calorimetric labels can be detected simply by observing the color associated with the label.

Other embodiments and uses will be apparent to one skilled in the art in light of the present disclosures.

EXAMPLE 1

Optimized 5T4 4-Color Diagnostic Assay

An optimized 4 channel assay was developed for identification of 5T4-positive CTCs. The CTCs were stained with four different stains and measured on four separate channels. For example, CTCs may be stained with anti-CK-AlexaFluor®555 (red); anti-CD45-AlexaFluor 488 ® (green); anti-5T4-AlexaFluor 660® (purple); and, the cell nuclei are stained blue with DAPI. Since AlexaFlour® fluorescent dyes (Invitrogen) are available in many colors alternative staining combinations are available.

Patients and Blood Sample Collection

Samples were collected from metastatic cancer patients in anti-coagulated blood tubes and processed within 24 hours. Blood samples were also drawn from normal controls.

Blood Sample Processing for CTC Detection

Blood samples were rocked for 5 minutes before a white blood cell (WBC) count was measured using the Hemocue WBC system (HemoCue, Sweden). Based upon the WBC count, a volume of blood was subjected to erythrocyte lysis (ammonium chloride solution). After centrifugation, nucleated cells were re-suspended in PBS and attached as a monolayer on custom made glass slides. The glass slides are the same size as standard microscopy slides but have a proprietary coating that allows maximal retention of live cells. Each slide holds approximately three million nucleated cells; thus the number of cells plated per slide depended on the patients' WBC count.

For CTC detection in cancer patients for this study, four slides were used as a test. The remaining slides created for each patient were stored at −80° C. for future experiments. Four slides were thawed from each patient, then cells were fixed with 2% paraformaldehyde, permeabilized with cold methanol, and non-specific binding sites were blocked with goat serum. Slides were subsequently incubated with monoclonal anti-pan cytokeratin antibody (Sigma), and CD45-Alexa fluorescent dye (Serotec) for 40 minutes at 37° C. After PBS washes, slides were incubated with goat anti-mouse antibody-Alexa Fluorescent dye (Invitrogen) for 20 minutes at 37° C. After PBS washes, slides were then incubated with anti-5T4 antibody-Alexa Fluorescent dye for 20 minutes at 37° C. Cells were counterstained with DAPI for 10 minutes and mounted with an aqueous mounting media.

Imaging and Technical Analysis

All four slides from each patient were scanned using a custom made fluorescent scanning microscope which was developed and optimized for fast, reliable scanning. Each slide was scanned entirely at 10× magnification in four colors and produced over 6900 images. The resulting images were fed to an analysis algorithm that identifies likely candidate CTCs based upon numerous measures, including cytokeratin intensity, CD45 intensity, 5T4 intensity as well as nuclear and cytoplasmic shape and size. A technical analyst then went through algorithm generated likely candidates and removed hits that are obviously not cells, such as dye aggregates.

Professional Analysis and Interpretation

All likely candidate CTCs were presented to a hematopathologist for analysis and interpretation through a web-based report where the hematopathologist includes or excludes each candidate cell as a CTC. Cells were classified as CTCs if they were cytokeratin positive, 5T4 positive, CD45 negative, contained an intact DAPI nucleus without identifiable apoptotic changes (blebbing, degenerated appearance) or a disrupted appearance, and are morphologically distinct from surrounding WBCs. Cells must have cytoplasm that is clearly circumferential and within which the entire nucleus is contained. The cytoplasm may show apoptotic changes such as blebbing and irregular density or mild disruption at the peripheral cytoplasmic boundary, but must not be so disrupted that its association with the nucleus is in question. The images are presented as digital images, with individual fluorescent channel viewing capability as well as a composite image. Each cell image was annotated with ancillary statistical data regarding relative nuclear size, fluorescent intensities, and comparative fluorescent intensities. Each CTC candidate was presented in a field of view with sufficient surrounding WBCs to allow for contextual comparison between cytomorphologic features of the cell in question versus the background WBCs.

Wright-Giemsa Staining

Coverslips were removed from fluorescently stained slides and rinsed in PBS. The slide was then flooded with Wright-Giemsa stain (Fisher Scientific, Kalamazoo, Mich.) for 3 minutes. 1.5 mL of phosphate buffer pH 6.8 (Fisher Scientific, Kalamazoo, Mich.) was added to the stain-covered slide and the stain and buffer were mixed together by gently rocking for 1 minute. The mixture was then allowed to stand on the slide for 2 more minutes before the slide is rinsed with deionized water and allowed to air dry.

The steps utilized in the CTC identification and characterization process of the optimized 5T4 4-color assay of the present invention are: (1) prepare the slides; (2) store the slides; (3) thaw and stain the slides; (4) scan the slides; (5) run algorithms; and, (6) technical analysis and reports.

The CTC assay was specifically developed with the clinical environment in mind as well as the need for early technology innovation and future automation. All laboratory processes follow strict standard operating procedures that have been optimized, tested, and validated. Data collection and candidate identification have been automated using specific interfaces that both enable the pathologist's decision making and subsequent tracking of these decisions.

This system promises to enable new research into the morphological classification molecular characterization of CTCs as well as applications for point-of-care screening, monitoring and management of cancer patients.

What is claimed:

1. A method for detecting 5T4-positive circulating tumor cells in a mammalian subject suspected of having 5T4-positive cancer and treating the mammalian subject comprising:

obtaining a sample of blood from the mammalian subject;

testing the sample of blood from the mammalian subject, wherein the sample of blood comprises a cell population;

mounting the sample of blood on a substrate;

detecting the presence of a nucleated cell using a first marker in the sample of blood, wherein the first marker is DAPI;

detecting the presence of expression of a second marker on a circulating tumor cell in the sample of blood, wherein the second marker is cytokeratin;

detecting the absence of expression of a third marker on a circulating tumor cell in the sample of blood, wherein the third marker is CD45;

detecting the presence of expression of a fourth marker on a circulating tumor cell in the sample of blood, wherein the fourth marker is human 5T4 antigen;

analyzing the first, second, third, and fourth markers in the cell population to identify and characterize the circulating tumor cells;

quantifying the expression of human 5T4 antigen on the circulating tumor cells, assigning an H-score category, and summing the percentage of cells in each H-score category multiplied by the value of the H-score category to generate an H-score, wherein the H-score is used to select a 5T4-positive cancer patient population; and administering an effective amount of an anti-5T4 antibody-drug conjugate to the mammalian subject in the 5T4-positive cancer patient population.

2. The method of claim 1, wherein detecting the presence of 5T4-positive circulating tumor cells in the sample of blood indicates the presence of early stage 5T4-positive cancer in the mammalian subject.

3. The method of claim 1, wherein detecting the absence of 5T4-positive circulating tumor cells in the sample of blood indicates a disease free state or a non-measurable disease state in the mammalian subject, wherein the disease is 5T4-positive cancer.

4. The method of claim 1, wherein the presence or absence of the circulating tumor cells in the sample of blood indicates therapy management during 5T4-positive cancer therapy or cancer recovery.

5. The method of claim 1, wherein the cell population is a mixed cell population.

6. The method of claim 1, wherein the substrate is a planar substrate, a micro fluidic device, or a cartridge that holds an enriched population of cells.

7. The method of claim 1, wherein mounting the sample on the substrate forms a biological monolayer.

8. The method of claim 1, wherein the first marker, the second marker, the third marker, or the fourth marker is detected using fluorescence.

9. The method of claim 1, wherein the first marker is used in analyzing the cell population by nuclear detail, nuclear contour, presence or absence of nucleoli, quality of cytoplasm, or quantity of cytoplasm.

10. The method of claim 9, further comprising analyzing the cell population by measuring intact cells with a high nuclear to cytoplasmic ratio, intact cells with a low nuclear to cytoplasmic ratio, early apoptotic cells, or late apoptotic cells, and identifying the circulating tumor cells and circulating tumor cell clusters.

11. The method of claim 1, further comprising a cytologic stain to identify the circulating tumor cell by morphology, size, or nuclear to cytoplasmic ratio.

12. The method of claim 11, wherein the cytologic stain is Wright-Giemsa stain.

13. The method of claim 1, further comprising analyzing the cell population by cell attachment to the substrate, scanning the cell population on the substrate, and imaging the cells by digital microscopy using relocation.

14. The method of claim 1, wherein detecting the presence of 5T4-positive circulating tumor cells in the sample of blood indicates the presence of a 5T4-positive cancer in a mammalian subject.

15. The method of claim 14, wherein the 5T4-positive cancer is selected from the group consisting of carcinomas of the bladder, breast, cervix, colon, endometrium, kidney, lung, esophagus, ovary, prostate, pancreas, skin, stomach, and testes.

16. The method of claim 1, wherein the analyzing of the first, second, third, and fourth markers in the cell population is utilized to determine the inclusion or exclusion of mammalian subjects for the treatment of 5T4-positive cancer.

* * * * *